(12) United States Patent
Van Beck-hoven et al.

(10) Patent No.: US 10,172,375 B2
(45) Date of Patent: Jan. 8, 2019

(54) COMPOSITIONS COMPRISING CARBOHYDRATES AND PEPTIDES WHICH COMPRISE TRYPTOPHAN

(75) Inventors: Rudolf Van Beck-hoven, Bavel (NL); Alexander Duchateau, Lanaken (BE); Luppo Edens, JL Rotterdam (NL); Franciscus Kleinherenbrink, Bangkok (TH); Joris Kloek, RK Gouda (NL); Andre L. Ross De, TB Delft (NL)

(73) Assignee: DSM IP ASSETS B.V., Heerlen (NL)

( * ) Notice: Subject to any disclaimer, the term of this patent is extended or adjusted under 35 U.S.C. 154(b) by 1996 days.

(21) Appl. No.: 12/989,858

(22) PCT Filed: Apr. 9, 2009

(86) PCT No.: PCT/EP2009/054315
§ 371 (c)(1),
(2), (4) Date: Jan. 7, 2011

(87) PCT Pub. No.: WO2009/132951
PCT Pub. Date: Nov. 5, 2009

(65) Prior Publication Data
US 2011/0166085 A1    Jul. 7, 2011

(30) Foreign Application Priority Data
Apr. 29, 2008  (EP) ................. 08155387

(51) Int. Cl.
| C07K 14/00 | (2006.01) |
| A61K 38/00 | (2006.01) |
| A61K 49/00 | (2006.01) |
| C07K 14/475 | (2006.01) |
| A23L 33/125 | (2016.01) |
| A23J 3/34 | (2006.01) |
| A23L 5/00 | (2016.01) |
| A23L 2/52 | (2006.01) |
| A23L 29/269 | (2016.01) |
| A23L 29/30 | (2016.01) |
| A23L 27/30 | (2016.01) |
| A23L 33/18 | (2016.01) |

(52) U.S. Cl.
CPC . *A23J 3/34* (2013.01); *A23L 2/52* (2013.01); *A23L 5/00* (2016.08); *A23L 27/33* (2016.08); *A23L 27/34* (2016.08); *A23L 29/274* (2016.08); *A23L 29/30* (2016.08); *A23L 29/35* (2016.08); *A23L 33/125* (2016.08); *A23L 33/18* (2016.08); *A23V 2002/00* (2013.01)

(58) Field of Classification Search
CPC ............ A61K 2300/00; A61K 31/7016; A23V 2002/00; A23V 2200/322; A23V 2250/065; A23V 2200/3202; A23V 2250/54; A23V 2250/70; A23L 1/2363; A23L 1/30; A23L 1/3053; A23L 1/2364; A23L 1/293; A23L 1/296; C12P 19/12; C07K 14/00
See application file for complete search history.

(56) References Cited

U.S. PATENT DOCUMENTS

| 5,189,016 | A | * | 2/1993 | Madsen et al. ............... 514/5.5 |
| 5,480,865 | A | * | 1/1996 | Kingham .................... 514/5.5 |
| 5,780,439 | A | * | 7/1998 | Mendy et al. ............... 514/5.6 |
| 5,872,100 | A | * | 2/1999 | Deghenghi .................. 514/11.3 |
| 7,064,104 | B2 | * | 6/2006 | Hayes et al. ................. 514/21.2 |
| 2003/0039739 | A1 | | 2/2003 | Wurtman et al. |
| 2004/0058866 | A1 | * | 3/2004 | Mallee et al. ................ 514/12 |
| 2009/0162483 | A1 | * | 6/2009 | Constantine ............ A23L 2/52 426/62 |
| 2009/0269443 | A1 | * | 10/2009 | van Beckhoven et al. .... 426/74 |
| 2010/0196559 | A1 | * | 8/2010 | Smulders et al. ............ 426/130 |
| 2011/0086803 | A1 | * | 4/2011 | De Roos et al. ............ 514/17.5 |
| 2011/0110919 | A1 | * | 5/2011 | Gerhardt et al. ............ 424/94.61 |
| 2011/0165287 | A1 | * | 7/2011 | Beckhoven Van et al. ...... 426/8 |
| 2011/0166085 | A1 | * | 7/2011 | Beck-hoven Van et al. ................. 514/21.9 |

FOREIGN PATENT DOCUMENTS

| EP | 0 951 842 | | 10/1999 | |
| FR | 2 777 751 | | 10/1999 | |
| JP | 2004-536030 | | 12/2004 | |
| JP | 2006-505592 | | 2/2006 | |
| JP | 2006-521106 | | 9/2006 | |
| JP | 2007-500755 | | 1/2007 | |
| WO | 02/46210 | | 6/2002 | |
| WO | 03/055322 | | 7/2003 | |
| WO | 2006/009448 | | 1/2006 | |
| WO | 2006/130567 | | 12/2006 | |
| WO | WO2006/130567 | * | 12/2006 | |
| WO | WO2007/095977 | * | 8/2007 | ............. A23L 1/054 |
| WO | 2008/052995 | | 5/2008 | |
| WO | WO 2008052995 A1 | * | 5/2008 | ............. C12P 21/06 |
| WO | WO2009011573 | * | 1/2009 | ............... A23L 2/66 |
| WO | WO2009057775 | * | 5/2009 | ........... A61K 31/198 |

OTHER PUBLICATIONS

International Search Report for PCT/EP2009/054315, dated Oct. 13, 2009.
Englyst et al., "Rapidly Available Glucose in Foods: An in Vitro Measurement that Reflects the Glycemic Response", American Journal of Clinical Nutrition, Bethesda, MD, US, vol. 69, No. 3, Mar. 1, 1999, pp. 448-454, XP002353205.
Beulens et al., "Alpha-Lactalbumin Combined with a Regular Diet Increases Plasma Trp-LNAA Ratio", Physiology and Behavior, Elsevier Science LTD., Oxford, GB, vol. 81, Jan. 1, 2004, pp. 585-593, XP002463927.
Lyons et al., "Serotonin Precursor Influenced by Type of Carbohydrate Meal in Healthy Adults", American Journal of Clinical Nutrition, vol. 47, No. 3, 1988, pp. 433-439, XP002501905.
Benton et al., "Carbohydrate, Memory, and Mood", *Nutrition Reviews*, May 2003, vol. 61, No. 5, pp. S61-S67.

* cited by examiner

*Primary Examiner* — Chang-Yu Wang
(74) *Attorney, Agent, or Firm* — Nixon & Vanderhye P.C.

(57) ABSTRACT

An edible composition comprising peptides rich in tryptophan, which edible composition further comprises a rapidly available glucose composition and a slowly available glucose composition.

11 Claims, No Drawings

COMPOSITIONS COMPRISING CARBOHYDRATES AND PEPTIDES WHICH COMPRISE TRYPTOPHAN

This application is the U.S. national phase of International Application No. PCT/EP2009/054315, filed 9 Apr. 2009, which designated the U.S. and claims priority to European Application No. 08155387.7, filed 29 Apr. 2008, the entire contents of each of which are hereby incorporated by reference.

FIELD OF THE INVENTION

The present invention relates to a formulation comprising tryptophan-containing peptides together with rapidly available glucose and slowly available glucose (i.e. "fast" and "slow" carbohydrates).

BACKGROUND OF THE INVENTION

Recently, there have been various reports on the benefit which tryptophan is believed to have on several aspects of human behaviour, mood, brain function, brain development, when such tryptophan is taken up by the brain. Examples of such reports are WO 99/55174, WO 00/42868, WO 2005/023017.

Tryptophan is an amino acid present in many proteins, like e.g. whey proteins, but also animal protein contains tryptophan. Tryptophan can be taken up in the blood, and from the blood into the brain, after ingestion of a protein which contains tryptophan. However, tryptophan is not the only amino acid taken up, and in fact when an average animal protein composition is ingested, the level of tryptophan taken up by the brain is so low due to competitive uptake of other amino acids that usually no significant effect can be observed attributable to tryptophan. Hence, most of the reports referred to above either use proteins or protein-fractions rich in tryptophan, or the free amino acid tryptophan (the latter optionally in combination with other free amino acids and/or proteins).

Use of tryptophan as free amino acids has disadvantages, in that food legislation in many countries limits the use of tryptophan as free amino acid in foodstuffs.

Tryptophan-rich proteins have natural limits to the level of tryptophan and its ratio to large neutral amino acids, which is relevant for uptake of tryptophan by the brain.

Recent insight is that peptides rich in tryptophan can be a good source to get sufficient tryptophan in the brain for the desired effects and may be easier applied in foodstuffs than free amino acids. Such peptides rich in tryptophan are preferably low in amino acids with which competition in uptake into the brain is believed to be high: the so-called large neutral amino acids (LNAA), which are: leucine, isoleucine, valine, tyrosine, phenylalanine (and depending on the definition of LNAA one uses also methionine). Hence, it is preferred to provide peptide preparations which contain a high level of tryptophan and have a high ratio tryptophan/LNAA. Methionine is considered not to have any beneficial metabolic effect in the context of this invention, and is thus for the purpose of this invention not considered as one of the LNAA.

EP 661004 discloses animal feed comprising tryptophan in combination with e.g. dextrin. Said composition is for maintaining growth and increase of body weight at high environmental temperatures when the animals have low appetite.

WO 2004/112803 discloses methods for managing the symptoms of premenstrual syndrome by providing a composition containing a protein having a high tryptophan/LNAA ratio, in combination with rapidly digestible carbohydrates.

WO 2006/130567 discloses methods for treating winter blues, seasonal affective disorder (SAD), and depressive disorders; and carbohydrate craving, weight gain, and mood symptoms associated with same, by administering to a subject a carbohydrate-rich composition with minimal protein content, or a carbohydrate-rich composition that contains tryptophan or a tryptophan-rich protein or peptide.

In US2003039739 compositions and methods of losing weight are described that are suitable for individuals susceptible to gastric hyperacidity or gastroesophageal reflux. The compositions include in part a snack food having two or more rapidly digestible carbohydrates, in which the foodstuff or an aqueous mixture of the foodstuff and water has a pH equal to or greater than about 6, and in which the snack is substantially protein-free. The experimental/test plan of the invention allocated the amounts of protein and carbohydrate differently at each meal and snack to ensure that following the lunch and dinner meals, the ratio of plasma tryptophan to that of the circulating large neutral amino acids is not decreased so that the ratio would be significantly elevated following the consumption of the carbohydrate-rich snack.

In WO02/46210 a method for increasing the level of tryptophan in whey protein hydrolysates is described. In the method used, whey is first hydrolysed at acidic pH by one or more acid proteases, preferably by a pepsin, rennin, acid fungal protease, chymosin, papain, bromelain, chymopapain or ficin. The preferred incubation conditions are between pH 1.5 and 3.5 and were chosen to generate peptides having a hydrophobic nature. The hydrolysis is deliberately carried out in such a way that the tryptophan residues become incorporated in large, hydrophobic peptides. Due to the fact that tryptophan is present in relatively large peptides, the tryptophan uptake into the blood will be retarded hereby limiting the application possibilities of the preparation as a food or beverage ingredient, especially in combination with other proteins. Another disadvantage of the use of such large peptides is that such peptides may give rise to allergic reactions. Such reactions to whey proteins are well known.

WO 2008/052995 relates to tryptophan-containing peptides, which further may contain carbohydrates.

Insulin may selectively promote uptake of the LNAA by various tissues, thus making more tryptophan available for uptake in the brain, as the LNAA compete with tryptophan for uptake in the brain. Thus, considerable levels of plasma insulin may be beneficial for the desired effects of tryptophan on the brain. Such desirable effects are related to the field of brain function, alertness, sleep, mood, concentration, and related issues. High plasma insulin levels may be promoted by presence of fast digestible carbohydrates together with a tryptophan containing composition, but such may lead to either a dip in blood glucose e.g. about 2 hours after ingestion and/or not being able to maintain considerable levels of blood glucose for e.g. 3-4 hours for the brain to have maximum benefit of the tryptophan and/or for optimal brain function, alertness, sleep, mood, concentration, cognition in general and related fields.

SUMMARY OF THE INVENTION

Hence, there was a need for a composition providing both tryptophan in a form which allows good uptake in the brain, which is from an industrially-widely available source, has a high tryptophan/LNAA ratio, a low allergenicity, and which may be used in formulations (e.g. for humans, like e.g. children) which may be beneficial for one or more of brain functioning, alertness, sleep, mood, concentration, cognition, and related fields.

This has now been achieved (at least in part) by a formulation comprising at least two different water-soluble, tryptophan-containing peptides (or peptide composition), and wherein the tryptophan/LNAA ratio of the formulation is at least 0.15, preferably between 0.15 and 1.8, which formulation further comprises a rapidly available glucose (RAG) composition and a slowly available glucose (SAG) composition, wherein the RAG composition and the SAG composition are present in the edible composition in dry weight ratio's of: RAG composition:SAG composition between 1:0.5 and 1:4, preferably between 1:0.8 and 1:3, more preferably between 1:1 and 1:3. It is these ranges that are believed to be both beneficial to tryptophan-uptake and to brainfunction, also over several hours.

Preferably, in the formulation according to this invention the weight ratio of the tryptophan-containing peptides:RAG composition is between 1:2 and 1:20, preferably between 1:3 and 1:15, more preferably between 1:3 and 1:8. It is these ranges that are believed to be both beneficial to tryptophan-uptake and to brainfunction, also over several hours.

It is also preferred herein that the formulation according to the present invention comprises 0.5 to 5% (preferably 0.8 to 3%) of dry weight of the tryptophan-comprising peptide composition on ready to consume product, as such allows easy formulation of consumable products, e.g. drinks, which have an acceptable volume and tryptophan concentration.

A further embodiment of this invention is a formulation comprising at least two different peptides selected from di- or tripeptides, whereby two peptides selected from di- or tripeptides are each present in an amount of at least 5 mol % of the total amount of di- and tripeptides, and in which more than 30 mol % of the total tryptophan is present as peptide bound tryptophan, and preferably more than 40 mol %, more preferably more than 50 mol %, even more preferably more than 60 mol %, still more preferably more than 70 mol % and most preferably more than 80 mol % of the peptide-bound tryptophan is present in the form of a di- or a tripeptide, preferably the formulation has a tryptophan/LNAA ratio of more than 0.15, preferably between 0.15 and 1.8, which formulation further comprises a rapidly available glucose (RAG) composition and a slowly available glucose (SAG) composition, wherein the RAG composition and the SAG composition are present in the formulation in dry weight ratio's of: RAG composition:SAG composition between 1:0.5 and 1:4, preferably between 1:0.8 and 1:3, more preferably between 1:1 and 1:3. In the above, it may further be preferred that the (dry) weight ratio of the tryptophan-containing peptides:RAG composition is between 1:2 and 1:20, preferably between 1:3 and 1:15, more preferably between 1:3 and 1:8. It is these amounts and ranges that are believed to be both beneficial to tryptophan-uptake and to brainfunction, also over several hours.

Rapidly available glucose (RAG) compositions and slowly available glucose (SAG) compositions are defined in the "detailed description of the invention".

It is also preferred herein that the formulation according to the present invention comprises 0.5 to 5% (preferably 0.8 to 3%) of dry weight of the tryptophan-comprising peptide composition on ready to consume product.

In the formulation according to the present invention, the tryptophan-comprising peptide composition preferably comprises tryptophan-containing peptides which can be obtained by process to produce a composition comprising a water-soluble, tryptophan-comprising peptide, preferably at least two water-soluble, tryptophan-containing peptides, and preferably having a tryptophan/LNAA ratio of more than 0.15, preferably between 0.15 and 1.8, which comprises hydrolyzing lysozyme, preferably hen eggs lysozyme, to prepare a hydrolysate having a Degree of Hydrolysis (DH) of between 5 and 45, and optionally removing part of the arginine or lysine containing peptides. Preferably, such tryptophan-comprising peptides for use in the formulation according to the present invention comprises AW or GNW, more preferably AW and GNW. Said hydrolysate has preferably a DH between 10 and 40. It is these amounts and ranges that are believed to be both beneficial to tryptophan-uptake and to brainfunction, also over several hours.

In the formulation according to the present invention, the tryptophan-comprising peptide composition is preferably in the form of a composition comprising at least two different water-soluble peptides and wherein the molar tryptophan/LNAA ratio of the composition is at least 0.15, preferably between 0.15 and 1.8. Preferably this tryptophan-comprising peptide composition comprises AW or GNW, preferably AW and GNW and most preferably AW and GNW whereby the molar ratio of AW to GNW is between 1 to 2 and 10 to 1, preferably between 1 to 2 and 5 to 1. Thus, in the present formulation the tryptophan-comprising peptide composition is preferably in the form of a composition of water-soluble peptides which are rich in tryptophan. Advantageously, in the present formulation the tryptophan-containing peptide composition preferably comprises at least two different di- or tripeptides, whereby two peptides selected from di- or tripeptides are present in an amount of at least 5 mol of the total amount of di- and tripeptides, and in which tryptophan-comprising peptide composition more than 30 mol %, preferably more than 40 mol %, more preferably more than 50 mol %, even more preferably more than 60 mol %, still more preferably more than 70 mol % and most preferably more than 80 mol % of the peptide-bound tryptophan is present in the form of a di- or a tripeptide, preferably the tryptophan-comprising peptide composition has a tryptophan/LNAA ratio of more than 0.15, preferably between 0.15 and 1.8. By peptide-bound tryptophan is meant a tryptophan which is present as amino acid in a peptide. It is these amounts and ranges that are believed to be both beneficial to tryptophan-uptake and to brainfunction, also over several hours.

The tryptophan-comprising peptide composition which is preferably used in the formulation according to the present invention is preferably a lysozyme hydrolysate or a purified lysozyme hydrolysate. Preferably, said lysozyme hydrolysate is particularly rich in arginine residues. Arginine does not belong to the group of large, neutral amino acids (LNAA's) but is known for its insulin stimulating effect. It has been found that the hydrolysate as herein disclosed can generate in vivo high blood plasma tryptophan/LNAA ratios. The tryptophan/LNAA ratios detected in blood plasma, were found to be higher than the tryptophan/LNAA ratio of the hydrolysate. Yet another advantage of the tryptophan-containing peptide composition herein described is that the tryptophan-containing peptides are very small so that even in combination with protein-rich products with less favorable tryptophan/LNAA ratios, the hydrolysate can immediately generate high blood plasma tryptophan/LNAA ratios. This thus makes such tryptophan-containing peptide composition well suitable in the formulation of the present invention. The tryptophan-containing peptide composition as used in the formulation of the present invention may further comprise free tryptophan. Preferably the hydrolysate of the tryptophan-containing peptide composition does not contain more than 1 wt % (on dry matter) of free tryptophan.

DETAILED DESCRIPTION OF THE INVENTION

Regarding slowly available glucose (SAG): this refers to a carbohydrate which is likely to be completely digested in the small intestine but at a slower rate than e.g. glucose or sucrose, resulting in lower blood glucose levels that are maintained for a longer time. On the other hand, rapidly available glucose (RAG) is a carbohydrate that is quickly hydrolysed, which results in high blood glucose concentrations, which are maintained for only a relatively short time.

Englyst et al. (Englyst KN, Englyst HN, Hudson GJ, Cole TJ, Cummings JH. Rapidly available glucose in foods: an in vitro measurement that reflects the glycaemic response. American Journal of Clinical Nutrition (1999) 69:448-54.) used an in vitro test that correlates significantly to the in vivo glucose curves. The in vitro measurement of RAG and SAG could predict the glycaemic response measured in human studies. Englyst et al. defined RAG in the in vitro situation by the amount of carbohydrate hydrolysed to glucose after 20 min (called G20). Also the amount hydrolysed was measured after 120 minutes (called G120). The amount hydrolysed during these 120 minutes was considered to be available for absorption in the small intestine. Anything hydrolysed after the 120 min was considered not available for absorption and considered resistant. The amount of carbohydrates hydrolysed between 20 and 120 min (i.e. G120-G20) was defined as SAG. For the purpose of this invention RAG and SAG are herein understood in the same way as defined by Englyst et al.

The in vitro technique used by Englyst et al for the measurement of RAG and SAG fractions on which the definition for RAG and SAG is relied upon herein, based on the measurement by HPLC of the glucose released from a test food during timed incubation with digestive enzymes under standardized conditions, is described in more detail below.

Materials RAG/SAG Determination

The polyethylene tubes used (50 mL) were from Falcon (Oxford, United Kingdom). Glass balls (1.5-cm diameter) were from Magnet Wholesale (Halesworth, United Kingdom). The shaking water bath was a Grant Instruments Ltd model SS-40-2 (Cambridge, United Kingdom). The bath was fitted with clips to hold 50-mL tubes exactly horizontal, fully immersed in the water, with the long axis of each tube in the direction of movement. The HPLC system was from Dionex (UK) Ltd, (Camberley, United Kingdom) and is described in detail below. Reagents were from Sigma (Poole, United Kingdom) or Merck (Poole, United Kingdom) unless stated otherwise.

The internal standard solution was 40 g arabinose/L in water with 50% saturated benzoic acid. The stock sugar mixture was 50 g glucose/L and 25 g fructose/L in water with 50% saturated benzoic acid. Sugars were dried to constant weight at reduced pressure over phosphorus pentoxide before use.

The enzymes used were pepsin from Sigma (catalog no. P-7000; St Louis), amyloglucosidase from Novo Nordisk (AMG 400 L type LP; Bagsvaerd, Denmark), pancreatin from Sigma (catalog no. P-7545), and invertase from Merck (catalog no. 390203D). The enzyme mixture was prepared on the day of use. For 18 samples, 3.0 g pancreatin was weighed into each of 6 centrifuge tubes and a magnetic stirring bar and 20 mL water was added to each. The pancreatin was suspended by vortex mixing and then mixed for 10 min on a magnetic stirrer. The tubes were centrifuged at 1500×g for 10 min; 15 mL of the cloudy supernate from each tube (90 mL total) was removed into a flask and 4 mL amyloglucosidase and 6 mL invertase were added and mixed well.

In vitro measurement of RAG, SAG, total glucose, and starch fractions Samples of food (containing <0.6 g carbohydrate) were weighed to the nearest milligram into 50-mL polypropylene centrifuge tubes. Internal standard solution (5 mL of 40 g arabinose/L) and 10 mL freshly prepared pepsin-guar gum solution (5 g pepsin/L and 5 g guar gum/L in 0.05 mol HCl/L) was added. The tubes were capped and the contents were vortex mixed and placed into a water bath at 37° C. for 30 min to allow hydrolysis of proteins by pepsin. Five milliliters 0.5 mol sodium acetate/L (equilibrated to 37° C.) was added to each tube to form a buffer at pH 5.2. Five glass balls were added and the tubes were capped and shaken gently to disperse the contents and then placed in the 37° C. water bath to equilibrate for a few minutes. In the shaking water bath, the glass balls function to mechanically disrupt the physical structure of the samples during the main incubation. The guar gum standardizes viscosity, keeps the sample in suspension, and prevents its sedimentation and excessive disruption by the glass balls.

One sample tube was removed from the 37° C. water bath and 5 mL enzyme mixture added. The tube was immediately capped and the contents mixed gently by inversion before it was secured horizontally in the 37° C. shaking water bath. The shaking action of the water bath was started at this time, which was taken as time zero for the incubation and was not interrupted until all the $G_{120}$ portions were collected (see below). The enzyme mixture was added to the rest of the sample tubes at 1-min intervals, to aid timing of incubations, and they were placed into the shaking water bath. Each tube was removed from the bath exactly 20 min after the enzyme mixture was added and 0.2 mL of the contents was added to 4 mL absolute ethanol and vortex mixed to stop the hydrolysis; this was the $G_{20}$ portion. The tube was returned to the shaking water bath immediately after the sample was taken. After another 100 min (a 120-min incubation), another 0.2 mL was added to 4 mL absolute ethanol and vortex mixed; this was the $G_{120}$ portion.

Potato starch and white wheat flour were included as reference materials in each batch of samples analyzed and 2 reagent blanks, one containing 4 mL stock sugar mixture, were included to correct for the sugar content of the enzyme preparations. The hydrolysis conditions were calibrated with potato starch, white wheat flour, and corn flakes reference materials. (Reference materials and enzymes are available from Englyst Carbohydrate Services Ltd, United Kingdom). Potato starch (air-dried, from Kartoffelmel Centralen, Herning, Denmark) has a high resistant starch content and was used to establish the optimum speed of the shaking water bath. If the $G_{120}$ value for the potato starch was too high, the stroke-speed was decreased and vice versa.

HPLC measurement of Sugars

Two sugar standards were used for calibration. Standard 1 was 1 mL and standard 2 was 10 mL of the stock sugar mixture, each made to 20 mL with water, to which 5 mL of the internal standard solution was added and mixed well; 0.2 mL of this mixture was then removed and added to tubes containing 4 mL absolute ethanol.

Before HPLC analysis, all the ethanolic fractions were centrifuged for 5 min at 1500×g at room temperature. The amount taken for analysis of the sugar standards and the $G_{20}$ and $G_{120}$ portions were 70 μL. The samples were placed into HPLC vials, 1 mL deionized water was added, and they were vortex mixed.

An autoinjector (model AS3500; Dionex) was used to inject 20 μL of the diluted ethanolic fractions. Sugar separation was achieved with an anion-exchange analytic column (Carbopac PA100; Dionex) and guard column (Carbopac PA10; Dionex) by using a gradient pump (model GP40; Dionex). Column switching and an anion-exchange guard column (Aminotrap; Dionex) were used to prevent amino acids and peptides from reaching the analytic column. The eluents, high-purity water and 200 mol NaOH/L (16 mL 50% NaOH solution/L high-purity degassed water), were degassed. The flow rate was 0.8 mL/min and the elution conditions are shown the following table:

| Sequence of elution conditions for the HPLC measurement of sugars | | |
|---|---|---|
| Switch position[1] | NaOH mmol/L | Time min |
| A | 10 | 0-3.5 |
| B | 70 | 3.6-14.0 |
| B | 200 | 14.1-15.0 |
| B | 10 | 15.1-20.0 |

[1]In switch position A, the flow is from Aminotrap (Dionex UK Ltd, Camberley, United Kingdom) to guard column to separation column.
In switch position B, the flow is from guard column to separation column to Aminotrap.
Sample injection is at time 0.1 min.

Monosaccharide detection was achieved with an electrochemical detector (model ED40; Dionex) with the following pulse potentials (E) and durations (t): $E_1$, 0.05 V; $t_1$, 400 ms; $E_2$, 0.75 V; $t_2$, 200 ms; $E_3$, 0.15 V; and $t_3$, 400 ms. The response time was 1 s, and the output on the detector was set at 300 nA. A data-handling system (DX-500; Dionex) was used to integrate and plot the results.

Values for RAG and SAG were calculated from the measured $G_{20}$ and $G_{120}$ values as follows:
RAG=G20
SAG=G120−G20

Preferred slowly available glucose (SAG) compositions in the formulation according to the present invention comprise one or more of: pullulan having a number average molecular weight of between 1000 and 45000 daltons (preferably 5000-40000 daltons), isomaltulose, trehalose, and/or mixtures thereof. Isomaltulose is preferred as a slow available glucose source, as these are commercially available sources.

Preferred rapidly available glucose (RAG) compositions in the formulation according to the present invention comprise one or more of glucose, sucrose, maltodextrine, starch, starch hydrolysate, dextrose, and/or mixtures thereof, as these are well known in food application and allow easy processing.

In the formulation according to the present invention, when it is a final formulation ready for consumption, it is preferred that the total amount of rapidly available glucose and slowly available glucose together is 5 to 20% (by weight) of the total formulation ready for consumption, preferably 7 to 15%, for e.g. ease of formulation and quality of end product (e.g. being not overly sweet)

The invention further relates to a product, in the form of a ready-to-drink liquid, which comprises 1-20% by weight of a formulation according to the present invention, as such allows easy formulation of consumable products, e.g. drinks, which have an acceptable volume and tryptophan concentration.

It is preferred that the peptides in the present formulation comprise AW or GNW, preferably AW and GNW. In such case, the molar ratio of AW to GNW is preferably between 1 to 2 and 10 to 1, more preferably between 1 to 2 and 5 to 1. It is these ratios that are believed to be both beneficial to tryptophan-uptake and to brainfunction, also over several hours.

In the formulation according to the present invention, the tryptophan-containing peptides are preferably obtainable by hydrolysing lysozyme, preferably a hen egg lysozyme.

In a further embodiment, the present invention relates to food, pet food, feed, drink, dietary supplement or neutraceutical compositions comprising the formulation according to the present invention.

Details of the tryptophan-containing peptide part of the present invention and the way to manufacture such are further set out in WO 2008/052995.

The tryptophan-comprising peptide composition preferably used in the formulation of the present invention provides a composition comprising tryptophan present in peptide form which is very suitable for giving an effective increase of the tryptophan/LNAA ratio in plasma in a very short time interval. The di- and tripeptides comprising tryptophan advantageously contribute to this increase. In one embodiment for the tryptophan-comprising peptide composition in the formulation of the present invention, lysozyme, preferably hen egg lysozyme is enzymatically (pre-)hydrolysed in an industrial process i.e. (hen egg) lysozyme is preferably provided in the form of a hydrolysate. Offered in the form of a hydrolysate, the gastrointestinal absorbtion of tryptophan containing peptides is greatly facilitated. In another embodiment, for the tryptophan-comprising peptide composition for the formulation of the present application, hen egg lysozyme is converted into a hydrolysate in which the levels of peptides comprising the positively charged arginine and lysine residues have been lowered. The latter hydrolysates are characterized by molecular tryptophan/LNAA ratios higher than 0.15. In yet another embodiment of the RTD formulation of the present application comprising the preferred tryptophan-comprising peptide composition, hen egg lysozyme is converted to a hydrolysate comprising a peptide population of which more than 50%, preferably more than 60%, more preferably more than 75% of the peptides present have a molecular weight below 500 Da. This with the proviso that the molecular weight distribution of the peptides present in the hydrolysate is carried out as described in the Materials & Methods section of the present application. Regarding the preferred tryptophan/LNAA ratio (of at least 0.15): the amino acid analysis of the hydrolysate is carried out as described in the Materials & Methods section of the present application.

A "protein" or "polypeptide" is defined herein as a chain comprising more than 30 amino acid residues.

A "peptide" or "oligopeptide" is defined herein as a chain of at least two (preferably 2 to 30) amino acids that are linked through peptide bonds. The terms "peptide" and "oligopeptide" are considered synonymous (as is commonly recognized) and each term can be used interchangeably as the context requires.

A "water-soluble" peptide is a peptide which is soluble in water at a pH of 5.0. All (oligo)peptide and polypeptide formulas or sequences herein are written from left to right in the direction from amino-terminus to carboxy-terminus, in accordance with common practice. The one-letter code of amino acids used herein is commonly known in the art and can be found in Sambrook, et al. (Molecular Cloning: A Laboratory Manual, $2^{nd}$ ed. Cold Spring Harbor Laboratory, Cold Spring Harbor Laboratory Press, Cold Spring Harbor, N.Y., 1989).

By protein hydrolysate, hydrolysate or hydrolysed protein is meant the product that is formed by enzymatic hydrolysis of the protein, an enriched hydrolysate being a fraction of the protein hydrolysate for example enriched in selected peptides or wherein peptides or polypeptides have been removed from the hydrolysate. So an enriched hydrolysate is preferably a mixture of peptides (or a peptide mixture). The peptide mixture as used in the present invention is therefore a mixture of at least two, preferably at least three, more preferably at least four tryptophan containing peptides. More preferably the mixture comprises a peptide population of which more than 50%, preferably even more than 60%, and most preferably more than 75% of the peptides present have a molecular weight below 500 Da. A tryphophan containing peptide means a peptide which comprises at least one L-tryphophan amino acid residue. The tryptophan/LNAA ratio represents the molar ratio of tryptophan relative to the levels of other Large Neutral Amino Acids (LNAA:, i.e. the sum of tyrosine, phenylalanine, leucine, isoleucine and valine). Except for the plasma tryptophan/LNAA ratio, the tryptophan/LNAA ratio relates only to peptide-bound amino acids. Thus free tryptophan, tyrosine, phenylalanine, leucine, isoleucine and valine are not taken into account in the tryptophan/LNAA ratio.

Peptide-bound amino acids are amino acids which are part of a peptide and not free amino acids.

The Tyr/BCAA ratio represents the molar ratio of tyrosine relative to the levels of branched chain amino acids (BCAA; i.e. the sum of leucine, isoleucine and valine). Preferably the Tyr/BCAA ratio is higher than 0.1, preferably higher than 0.12.

The tryptophan-comprising peptide composition preferably used in the formulation of the present invention can be produced by a process as disclosed herein, and has a tryptophan yield of more than 30% on protein tryptophan basis and generates a water soluble peptide composition comprising tryptophan. The fact that the larger part of the tryptophan residues is encompassed in di- and tripeptides, implies an immediate uptake into the blood stream. Said tryptophan-comprising peptide composition preferably used in the formulation of the present invention may also generate higher blood plasma tryptophan/LNAA ratios than the tryptophan/LNAA ratio of the actual hydrolysate. Finally, the tryptophan-comprising peptide composition preferably used in the formulation of the present invention is also characterized by a very low antigenicity.

In tryptophan-comprising peptide composition preferably used in the formulation of the present invention hen egg lysozyme is preferably used as a convenient substrate for providing preparations with a high tryptophan/LNAA ratio. Lysozyme is present in egg white in a concentration of 3-4%. By taking advantage of its exceptionally high isoelectric point, lysozyme is industrially isolated from egg white using a simple cation chromatographic purification step. The resulting product is almost pure and this industrially available product has a molecular tryptophan content of 7.8% and molecular tryptophan/LNAA ratio of at least 0.15. Thus, pure lysozyme has a tryptophan/LNAA ratio that is significantly higher than pure alpha-lactalbumin and or beta-lactoglobulin. Therefore, the lysozyme hydrolysates for the tryptophan-comprising peptide composition preferably used in the formulation (and thus the tryptophan-comprising peptide composition themselves preferably used in the formulation) of the present invention may have a molar tryptophan/LNAA ratio which is higher than 0.15, more preferably the tryptophan/LNAA ratio is higher than 0.20, even more preferably the tryptophan/LNAA ratio is higher than 0.23, still more preferably the tryptophan/LNAA ratio is higher than 0.25 and most preferably the tryptophan/LNAA ratio is higher than 0.30. In general the molar tryptophan/LNAA ratio is below 3.0. As such lysozyme presents a preferred starting point for tryptophan containing peptides or compositions. Lysozyme (EC3.2.1.17) is an enzyme able to hydrolyse specific peptidoglycan bonds in bacterial cell walls leading to cell lysis. It is these ratios that are believed to be both beneficial to tryptophan-uptake and to brainfunction, also over several hours, and still can be achieved.

The hydrolysate preferably used for the tryptophan-comprising peptide composition in the formulation according to the present invention is also effective if incorporated into high protein containing food matrices as presented by, for example, dairy products. This is quite surprising as protein containing food matrices represent high LNAA loads and thus can be expected to reduce the effect of products with high tryptophan/LNAA ratios. A possible explanation for this unexpected phenomenon is that the usual food products incorporate intact, rather than extensively hydrolyzed proteins. The majority of the tryptophan and tyrosine incorporating peptides of the preferred tryptophan-comprising peptide composition has a molecular weight below 500 Da. In view of the very high molecular weight of tryptophan (MW=186) and tyrosine (MW=163) and the fact that only very low levels of free tryptophan are present, the implication is that the majority of these peptides will be tri- or di-peptides.

In a preferred way, the lysozyme, preferably hen egg lysozyme is enzymatically (pre-) hydrolysed in an industrial process i.e. (hen egg) lysozyme is preferably provided in the form of a hydrolysate or an enriched hydrolysate. Offered in the form of such an (enriched) hydrolysate, the intestinal absorbtion of tryptophan containing peptides is greatly facilitated. In another embodiment of the present application, hen egg lysozyme is converted to a hydrolysate or enriched hydrolysate comprising a tryptophan comprising peptide population of which more than 50%, preferably more than 60%, more preferably more than 75% of the peptides present have a molecular weight below 500 Da. Preferably such an (enriched) hydrolysate does not contain more than 1 wt % (on dry matter) of free tryptophan. The molecular weight analysis of the tryptophan comprising peptides present in the hydrolysate is carried out as described in the Materials & Methods section.

It may further be preferred that for the tryptophan-comprising peptide composition preferably used in the formulation of the present invention, the (hen egg) lysozyme hydrolysate is fractionated in order to increase the tryptophan content of a fraction of the hydrolysate. This fraction or enriched hydrolysate has preferably an increased tryptophan/LNAA ratio as compared to the hydrolysate before fractionation. The enrichment of the hydrolysate or enriched hydrolysate with additional free tryptophan, also forms part of the present invention. In a preferred option for preparing such an enriched hydrolysate, use is made of the observation that lysozyme incorporates an unusual high amount of the basic arginine and lysine residues. Surprisingly and as a result of selected enzyme incubation conditions i.e. choosing an endoprotease having the right cleavage preference (such as subtilisin) in combination with incubation conditions that yield a high amount of di- and tri-peptides incorporating tryptophan but almost no arginine or lysine residues, an enriched lysozyme hydrolysate according to the invention can be produced. Thus, LNAA-containing peptides incorporating arginine or lysine residues can be separated from tryptophan containing peptides that do not have such basic residues. For example, by adjusting the pH of the hydrolysate to a value between 4 and 6, more preferably between 5.0 and 5.5, peptides without such a basic residue will have no charge and, therefore, a reduced hydrophilicity. These features can be used e.g. in a chromatographic or another separation process to selectively remove a large proportion of the arginine or lysine containing peptides. As a result, the content of tryptophan-containing peptides is dramatically increased and optionally the tryptophan/LNAA ratio of this enriched hydrolysate. Charged arginine or lysine incorporating peptides can be removed by known techniques such as ion chromatography, hydrophobic interaction chromatography or electrodialysis. A practical background on the use of such characteristics in the chromatographic separation of the relevant peptides, can be found in a.o. the Protein Purification Handbook (issued by Amersham Pharmacia Biotech, nowadays GE Healthcare Bio-Sciences, Diegem, Belgium). In an even more advanced purification route towards preparations that combine a high tryptophan content with a high tryptophan/LNAA ratio, the presence of amino acids with acid side groups such as glutamate (Glu) and aspartate (Asp) residues in lysozyme is advantageously used. In this approach the pH of the lysozyme hydrolysate according to the invention is first adjusted to 3.0 and then chromatographed over a cation resin. At this pH value, peptides incorporating a Glu or Asp will run through the column, other peptides will bind. A subsequent elution with a pH 5 buffer will desorb all bound peptides without a lysine or an arginine residue as described. The majority of the tryptophan containing peptides will be in this desorbed fraction. The remaining bound peptides can then be removed from the column by elution with a buffer with an even higher pH value.

Although for the preparation of the tryptophan-comprising peptide composition preferably used in the formulation of the present invention preferably ion exchange chromatography and/or hydrophobic interaction chromatography are used, other suitable chromatrographic separation methods comprising affinity chromatography and size exclusion chromatography also are available. The recovery of the tryptophan enriched peptides from resulting aqueous fractions can be done by methods that are known in the art. In order to obtain concentrated and shelf stable products, the recovery preferably incorporates an evaporation and (spray) drying step. Also nanofiltration and extraction processes involving organic solvents followed by evaporation/precipitation steps present options for the desired purification. The recovery of the tryptophan enriched peptides from organic solvents is preferably carried out by evaporation of the solvent.

Despite the fact that lysozyme turns out to be highly resistant to proteolytic hydrolysis under physiological conditions, i.e. at an acid pH using pepsin, trypsin and chymotrypsin as proteases, lysozyme hydrolysates as are preferably used in the formulation of the present invention also can be obtained under such less favorable acid conditions. However, under such conditions relatively harsh incubation conditions are required, such as much higher enzyme concentrations, higher temperatures and optionally additional endoproteases. A lysozyme hydrolysate obtained by incubating lysozyme at an alkaline pH with subtilisin was found particularly rich in the Ala-Trp (AW) dipeptide.

In the composition according to the present invention the tryptophan-comprising peptide composition preferably comprises a peptide composition having a tryptophan to LNAA (weight) ratio of at least 0.1, preferably at least 0.15, more preferably 0.15-1.8, and preferably such is obtained by a process which comprises hydrolysing lysozyme, more preferably hen eggs lysozyme, to prepare a hydrolysate having a DH of between 5 and 45, and optionally removing part of the arginine or lysine containing peptides. In this, the tryptophan-comprising peptide composition preferably comprises AW or GNW, preferably AW and GNW (wherein the molar ratio of AW to GNW is preferably between 1 to 2 and 10 to 1, more preferably between 1 to 2 and 5 to 1), and which composition further comprises a rapidly available glucose (RAG) composition (preferably comprising one or more of pullulan having a number average molecular weight of between 1000 and 45000 daltons (preferably 5000-40000 daltons), isomaltulose, trehalose, and/or mixtures thereof, most preferably isomaltulose) and a slowly available glucose (SAG) composition (preferably comprising one or more of glucose, sucrose, maltodextrine, starch, starch hydrolysate, dextrose, and/or mixtures thereof), wherein the RAG composition and the SAG composition are present in the formulation in dry weight ratio's of: RAG composition: SAG composition between 1:0.5 and 1:4, preferably between 1:0.8 and 1:3, more preferably between 1:1 and 1:3, and optionally also the weight ratio of the tryptophan-containing peptides:RAG composition is between 1:2 and 1:20, preferably between 1:3 and 1:15, more preferably between 1:3 and 1:8. Herein, when the formulation is ready for consumption it is preferred that the total amount of rapidly available glucose and slowly available glucose together is 5 to 20% (by weight) of the total formulation ready for consumption, preferably 7 to 15%. It is also preferred herein that the formulation according to the present invention comprises 0.5 to 5% (preferably 0.8 to 3%) of dry weight of the tryptophan-comprising peptide composition on ready to consume product. It is these amounts, ratios and ranges that are believed to be both beneficial to tryptophan-uptake and to brainfunction, also over several hours, and still can be achieved.

In the formulation according to the present invention, it may be preferred that the tryptophan-comprising peptide preparation comprises at least two different peptides selected from di- or tripeptides, whereby two peptides selected from di- or tripeptides are each present in an amount of at least 5 mol % of the total amount of di- and tripeptides, and in which more than 30 mol % of the total tryptophan is present as peptide bound tryptophan, and preferably more than 40 mol %, more preferably more than 50 mol %, even more preferably more than 60 mol %, still more preferably more than 70 mol % and most preferably more than 80 mol % of the peptide-bound tryptophan is present in the form of a di- or a tripeptide, preferably the composition has a tryptophan/LNAA ratio of more than 0.15, preferably between 0.15 and 1.8, and which composition further comprises a rapidly available glucose (RAG) composition (preferably comprising one or more of: pullulan having a number average molecular weight of between 1000 and 45000 daltons (preferably 5000-40000 daltons), isomaltulose, trehalose, and/or mixtures thereof, most preferably isomaltulose) and a slowly available glucose (SAG) composition (preferably one or more of glucose, sucrose, maltodextrine, starch, starch hydrolysate, dextrose, and/or mixtures thereof), wherein the RAG composition and the SAG composition are present in the formulation in dry weight ratio's of: RAG composition: SAG composition between 1:0.5 and 1:4, preferably between 1:0.8 and 1:3, more preferably between 1:1 and 1:3, and optionally also the weight ratio of the tryptophan-containing peptides:RAG composition is between 1:2 and 1:20, preferably between 1:3 and 1:15, more preferably between 1:3 and 1:8. Herein, when the formulation is ready for consumption it is preferred that the total amount of rapidly available glucose and slowly available glucose together is 5 to 20% (by weight) of the total formulation ready for consumption, preferably 7 to 15%. It is also preferred herein that the formulation according to the present invention comprises 0.5 to 5% (preferably 0.8 to 3%) of dry weight of the tryptophan-comprising peptide composition on ready to consume product. It is these amounts, ratios and ranges that are believed to be both beneficial to tryptophan-uptake and to brainfunction, also over several hours, and still can be achieved.

The invention further relates to a formulation wherein it is preferred that it comprises 0.5 to 5% (preferably 0.8 to 3%) of dry weight of the tryptophan-comprising peptide composition on ready to consume product.

The invention further relates to a food, pet food, feed, dietary supplement or neutraceutical composition comprising the formulation as herein disclosed. Such products may be e.g. in the form of a ready-to-drink liquid. Such products may typically comprise 1-20%, more preferably 2-15%, by weight of a formulation (i.e. comprising the peptides, RAG and SAG) according to the present invention.

Materials and Methods

Materials

Subtilisin under the commercial name of "Protex 6L" was obtained from Genencor (Leiden, The Netherlands), pepsin from Sigma and the mixture of trypsin/chymotrypsin (Porcine PEM) from Novozymes (Bagsvaerd, Denmark). Lysozyme was obtained as Delvozyme L (22% dry matter) from DSM Food Specialities (Delft, The Netherlands).

SDS-PAGE

The purity of the lysozyme preparations used was checked by SDS-PAGE. All materials used for SDS-PAGE and staining were purchased from Invitrogen (Carlsbad, Calif., US). Samples were prepared using SDS buffer according to manufacturers instructions and separated on 12% Bis-Tris gels using MES-SDS buffer system according to manufacturers instructions. Staining was performed using Simply Blue Safe Stain (Collodial Coomassie G250). Prior to hydrolysis the lysozyme appeared as a single band with a molecular weight of approx. 14 kDa on the gel.

LC/MS/MS Analysis

HPLC using an ion trap mass spectrometer (Thermo Electron, Breda, the Netherlands) coupled to a P4000 pump (Thermo Electron, Breda, the Netherlands) was used to determine the presence of tryptophan containing peptides (mainly di- and tri peptides) in the enzymatic protein hydrolysates produced by the process according to the invention. The peptides formed were separated using an Inertsil 3 ODS 3, 3 µm, 150*2.1 mm column (Varian Belgium, Belgium) in combination with a gradient of 0.1% formic acid in Milli Q water (Millipore, Bedford, Mass., USA; Solution A) and 0.1% formic acid in acetonitrile (Solution B) for elution. The gradient started at 100% of Solution A, kept here for 10 minutes, increasing linear to 20% B in 25 minutes and immediately going to the starting conditions, and kept here 15 minutes for stabilization. The injection volume used was 50 microliter, the flow rate was 200 microliter per minute and the column temperature was maintained at 55° C. The protein concentration of the injected sample was approx. 50 micrograms/milliliter. Identification of the peptides of interest is based on the retention time, protonated molecule and by using dedicated MS/MS for the peptides of interest, using optimal collision energy of about 30%.

Quantification of Specific Tryptophan Containing Peptides is Performed by Using an External Standard Method.

The tetra peptide VVPP (M=410.2) was used to tune for optimal sensitivity in MS mode and for optimal fragmentation in MS/MS mode, performing constant infusion of 5 µg/ml, resulting in a protonated molecule in MS mode, and an optimal collision energy of about 30% in MS/MS mode, generating a B- and Y-ion series. Prior to LC/MS/MS the enzymatic protein hydrolysates were centrifuged at ambient temperature and 13000 rpm for 10 minutes and the supernatant was diluted 1:100 with demineralised water filtered through Millipore water filtration equipment (MilliQ water).

Degree of Hydrolysis

The Degree of Hydrolysis (DH) as obtained during incubation with the various protolytic mixtures was monitored using a rapid OPA test (Nielsen, P. M.; Petersen, D.; Dambmann, C. Improved method for determining food protein degree of hydrolysis. *Journal of Food Science* 2001, 66, 642-646).

Kjeldahl Nitrogen

Total Kjeldahl Nitrogen was measured by Flow Injection Analysis. Using a Tecator FIASTAR 5000 Flow Injection System equipped with a TKN Method Cassette 5000-040, a Pentium 4 computer with SOFIA software and a Tecator 5027 Autosampler the ammonia released from protein containing solutions was quantitated at 590 nm. A sample amount corresponding with the dynamic range of the method (0.5-20 mg N/l) was placed in the digestion tube together with 95-97% sulphuric acid and a Kjeltab subjected to a digestion program of 30 minutes at 200 degrees C. followed by 90 minutes at 360 degrees C. After injection in the FIASTAR 5000 system the nitrogen peak is measured from which the amount of protein measured can be inferred.

Molecular weight distribution of peptides and proteins present in hydrolysates. Analysis of the peptide size distribution of protease treated protein samples was done on an automated HPLC system equipped with a high pressure pump, an injection device able to inject 10-100 microliter sample and a UV detector able to monitor the column effluent at 214 nm.

The column used for this analysis was a Superdex Peptide HR 10/300 GL (Amersham) equilibrated with 20 mM Sodium Phosphate/250 mM Sodium Chloride pH 7.0 buffer. After injecting a sample (typically 50 microliter) the various components were eluted from the column with buffer in 90 min at a flow rate of 0.5 ml/min. The system was calibrated using a mixture of cytochrome C (Mw 13 500 Da), aprotinin (Mw 6510 Da) and tetra-glycine (Mw 246 Da) as molecular weight markers.

The following Examples illustrate the invention further.

EXAMPLES

Example 1

Hydrolysing Lysozyme Using Protex and Identity of the Peptides Formed.

A solution containing 10% (w/w) pure lysozyme was adjusted to pH 8.2 using NaOH and heated to 52 degrees C. Hydrolysis was started by adding 25 microliter of Protex/g of protein present. Under continuous stirring and maintaining the pH at 8.2, the hydrolysis was continued for 5.5 hours to yield an almost clear solution without a visible precipitate. After a heating step to inactivate the Protex activity, a sample was taken for DH analysis. The DH of the solution turned out to be almost 30%. The heat treated solution was ultrafiltered over a 10 kDa filter to yield a completely clear liquid. This clear liquid was used for LC/MS analysis, for molecular weight distribution of peptides and proteins present as well as for ion exchange chromatography.

To get an impression of the molecular weight distribution of peptides and proteins present, the clear liquid was subjected to a molecular size analysis as described in the Materials & Methods section. The results obtained clearly indicate that almost all peptides incorporating amino acids with an aromatic side chain (i.e. tryptophan, tyrosine and phenylalanine) have a molecular weight below 500 kDa. In view of the high molecular weight of these amino acids, the implication is most of these small peptides are either tri-or dipeptides.

LC/MS analysis was carried out according to the procedure as described in the Materials & Methods section. By selecting for those peptides containing a tryptophan ("W"), peptides AW, GNW, WIR, NAW, WVA, VAW, AWR, SLGNW and minor quantities of WW and SRWW could be detected. The level of free tryptophan in the hydrolysate after incubation was established to represent less than 1% of the total (lysozyme) tryptophan present.

As di- and tripeptides are readily absorbed by peptide transporters present in the intestinal wall, there is little doubt that tryptophan residues present in such peptides will be rapidly absorbed and lead to increased plasma tryptophan levels upon oral intake of the present lysozyme hydrolysate.

Example 2

Increasing the Tryptophan Content of the Hydrolysate.

Lysozyme incorporates a surprising high amount of the basic arginine and lysine residues. Furthermore the lysozyme molecule incorporates a significant number of the acid glutamate and aspartate residues. This data has been used to devise an innovative and elegant purification route towards hydrolysates featuring high tryptophan/LNAA ratios. Essential requirement for this purification route is, however, that only very few of the tryptophan residues show up in peptides also containing either an arginine or lysine residue or a glutamate or aspartate residue. As shown in Example 1, the specific hydrolysis route used here yields only few trytophan containing peptides containing an arginine residue and no peptides containing a lysine, glutamate or aspartate residue.

Theory predicts that a maximal charge difference between peptides with and without a glutamate or aspartate residue can be achieved around pH 3. A maximal charge difference between peptides with and without an arginine or lysine residue, can be achieved around pH 5.

To illustrate the selective power of this approach, a lysozyme hydrolysate was prepared according to the procedure specified in Example 1. Then, the pH of the hydrolysate was adjusted to pH 3.1 using acetic acid and approximately 0.5 gram of protein was applied to a 15 ml bed volume of SP Sepharose FF (GE Healthcare, Diegem, Belgium) column equilibrated with 20 mm sodium citrate pH 3.1. After washing the column with one column volume of the sodium citrate buffer to remove the majority of the peptides incorporating a glutamate or aspartate, the elution buffer was changed to a 20 mm sodium citrate buffer pH 5.1. During washing of the column with three column volumes of the latter buffer, a range of tryptophan containing peptides was eluted. According to LC/MS analysis, the dipeptide AW was present in large amounts as well as the tripeptides GNW, NAW, WVA, VAW and a small amount of the pentapeptide SLGNW. Amino acid analysis of the various pH 5.1 fractions showed that selective pooling yielded a solution having a molecular tryptophan/LNAA ratio of 1.75 and a tryptophan yield of almost 30%. A less selective pooling yielded a solution with a molecular Trp/LNAA ratio of 0.4 and a tryptophan yield of 70%. Subsequently, the column was washed with three column volumes 20 mM sodium citrate pH 7.1. According to the LC/MS data, this step eluted arginine containing peptides WIR, AWIR and, surprisingly, peptide WW. A final washing of the column with 1 M of NaOH, water and 1M of acetic acid prepared the column for a next run.

Example 3

Large Scale Lysozyme Hydrolysis.

In larger scale lysozyme hydrolysis procedures, essentially the procedure as described in Example 1 was followed with some minor modifications. A solution containing 7.3% (w/w) pure lysozyme was heated to 65 degrees C. after which the pH was adjusted to pH 8.2 using NaOH. Hydrolysis was started by adding 25 microliter of Protex 6 L/g dry matter. Under continuous stirring and maintaining the pH at 8.2 and the temperature at 53 degrees C., the hydrolysis was continued for 2 hours. Then the pH value was increased to 9.0 and incubation was pursued for another 3.5 hours to yield a solution with some precipitate. Then the pH of the solution was lowered to 4.5 and the solution was cooled to below 4 degrees C. To obtain a completely clear product, the liquid was filtered over a Z 2000 filter (Pall) and subsequently excess water and salt was removed via nanofiltration. The resulting concentrate was then subjected to an UHT treatment of 7 seconds at 120 degrees C., evaporated and finally spray dried to obtain the lysozyme hydrolysate in a dry form. The product thus obtained has a molar tryptophan/LNAA ratio of about 0.19.

Example 4

A peptide composition comprising peptides with tryptophan was prepared along the lines as set out in example 3. The product obtained was an aqueous liquid having a peptide level of about 83%, a peptide-bound tryptophan content of about 5.5%, and having a TRP/LNAA ratio of about 0.19. Said product had the appearance of a light yellow powder, and gave, upon dissolving as 1% in water, a solution having a pH of about 4.3.

With the above peptide preparation drinks could be prepared having the composition as in table 1 below (dry weight % of the ingredients in the aqueous base. Remainder can be water). A process to prepare these compositions can be:
 preparing a pre-mix of all ingredients in water,
 stirring such for 10 minutes, and adjusting the pH towards the end of stirring, where desired,
 optionally homogenising by a high pressure homogeniser.

TABLE 1

|  | Example 4a | Example 4b |
|---|---|---|
| Peptide preparation containing tryptophan (wt. %) | 1.14 | 1.14 |
| Skim milk powder (%) | 2.1 | 2.1 |
| Carrageenan (wt. %) | 0.02 | 0.02 |
| Maltodextrin (wt. %) | 1.0 | 1.0 |
| Sucrose (wt. %) | 4.6 | 4.6 |
| Isomaltulose (wt. %) | 6 | 10 |

The invention claimed is:

1. A formulation comprising at least two different water-soluble, tryptophan-containing peptides, which are di- or tripeptides comprising the peptides alanine-tryptophan (AW) or glycine-asparagine -tryptophan (GNW), and
wherein the tryptophan/Large Neutral Amino Acid ratio of the formulation is at least 0.15, which composition further comprises a rapidly available glucose (RAG) composition and a slowly available glucose (SAG) composition,
wherein the RAG composition and the SAG composition are present in the formulation in dry weight ratio's of: RAG composition : SAG composition between 1:0.5 and 1:4 ,
wherein the slowly available glucose (SAG) composition comprises one or more of: pullulan having a number average molecular weight of between 1000 and 45000 daltons, isomaltulose, and/or mixtures thereof, and
wherein the rapidly available glucose (RAG) composition comprises one or more of glucose, sucrose, maltodextrine, starch, starch hydrolysate, dextrose, and/or mixtures thereof .

2. The formulation according to claim 1, wherein the weight ratio of the tryptophan-containing peptides: RAG composition is between 1:2 and 1:20.

3. The formulation according to claim 1, wherein the molar ratio of Alanine-Tryptophan to Glycine-Asparagine-Tryptophan is between 1 to 2 and 10 to 1.

4. A formulation comprising at least two different peptides selected from di- or tripeptides, whereby two peptides selected from di- or tripeptides are each present in an amount of at least 5 mol % of the total amount of di- and tripeptides, and in which more than 30 mol % of the total tryptophan is present as peptide bound tryptophan, and more than 40 mol % of the peptide-bound tryptophan is present in the form of a di- or a tripeptide, the formulation has a tryptophan/Large Neutral Amino Acid ratio of more than 0.15, which formulation further comprises a rapidly available glucose (RAG) composition and a slowly available glucose (SAG) composition, wherein the RAG composition and the SAG composition are present in the formulation in dry weight ratio's of: RAG composition: SAG composition between 1:0.5 and 1:4;
wherein the weight ratio of the tryptophan-containing peptides: RAG composition is between 1:2 and 1:20.

5. The formulation according to claim 1, wherein the tryptophan-containing peptides are obtainable by hydrolysing lysozyme.

6. The formulation according to claim 1, wherein it is ready for consumption and wherein the total amount of rapidly available glucose and slowly available glucose together is 5 to 20% (by weight) of the total formulation ready for consumption.

7. The formulation according to claim 1, comprising 0.5 to 5% of dry weight of the tryptophan-comprising peptide composition on ready to consume product.

8. A food, pet food, feed, drink, dietary supplement or neutraceutical composition comprising the formulation according to claim 1.

9. A product according to claim 7, in the form of a ready-to-drink liquid.

10. The product according to claim 8, which comprises 1-20% by weight of the formulation.

11. The formulation according to claim 1 wherein the pullulan has a number average molecular weight of between 5000-40000 daltons.

* * * * *